United States Patent [19]

Desmurs et al.

[11] Patent Number: 5,206,407
[45] Date of Patent: Apr. 27, 1993

[54] PROCESS FOR THE PREPARATION OF SECONDARY OF TERTIARY DIALKYL DICARBONATE

[75] Inventors: Jean Desmurs, Communay; Serge Ratton, Germain-en-Laye, both of France

[73] Assignee: Rhone-Poulenc Chimie, Cedex, France

[21] Appl. No.: 594,155

[22] Filed: Oct. 9, 1990

[30] Foreign Application Priority Data

Oct. 9, 1989 [FR] France .................. 89 13140

[51] Int. Cl.$^5$ .............................................. C07C 68/04
[52] U.S. Cl. .................................................... 558/276
[58] Field of Search ........................................ 558/276

[56] References Cited

U.S. PATENT DOCUMENTS

3,078,294 2/1963 Howe et al. ..................... 558/276
4,929,748 5/1990 Franklin .......................... 558/276

*Primary Examiner*—Arthur C. Prescott
*Attorney, Agent, or Firm*—Finnegan, Henderson, Farabow, Garrett & Dunner

[57] ABSTRACT

A process for the preparation of a secondary or tertiary dialkyl dicarbonate. An alkali metal salt of an alkyl pyrocarbonate is contacted with $(CO)_nX_2$ wherein X is defined as a leaving group and n is an integer from 1 to 2, in the presence of a complexing agent.

54 Claims, No Drawings

PROCESS FOR THE PREPARATION OF SECONDARY OF TERTIARY DIALKYL DICARBONATE

The present invention relates to a new process for the preparation of secondary or tertiary dialkyl dicarbonate. It relates more particularly to the preparation of di-tert-butyl dicarbonate utilizing a compound $(CO)_nX_2$, defined below, such as phosgene, diphosgene or triphosgene Secondary and tertiary dialkyl dicarbonates are useful in the preparation of peptides It is well-known to prepare di-tert-butyl dicarbonate, often called $BOC_2O$ from tert-butyl pyrocarbonate and phosgene. This method is described by J. H. Howe in the *Journal of Organic Chemistry* 27:1901 (1962).

It is also known to prepare di-tert-butyl dicarbonate by condensing tert-butyl carbonate with an acid chloride in a mixture of toluene and dimethylformamide. This method is described in the paper published by Pozdev, Smirnova, Podgornova, Zentsova and le Kalei in *Zhurnal Organicheskoi Khimii*, Vol. 15: 106–109 (1979) and translated in the *Journal of Organic Chemistry USSR* 1979, page 95. Reproduction of these tests resulted in insufficient di-tert-buty dicarbonate yields.

The present invention has made it possible to prepare good yields of secondary or tertiary dialkyl dicarbonate by directly utilizing $(CO)_nX_2$, defined below, such as diacid dichloride or an equivalent substance.

The process comprises condensing secondary or tertiary alkyl (alkyl is defined as in *Duval's Chemical Dictionary*, 2nd Edition to include any compound derivable from alcohol by splitting off the alcoholic function and, of course, includes aralkyl) pyrocarbonate, and particularly the alkali metal salt of the pyrocarbonate with a compound of the formula $CO)_nX_2$, defined below, in the presence of at least one complexing agent.

The reaction can be expressed diagrammatically as follows:

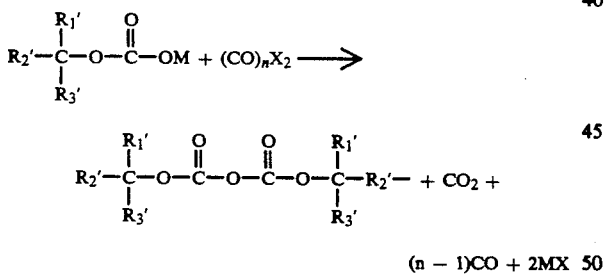

$$(n - 1)CO + 2MX$$

wherein X represents a leaving group preferably selected from an acyloxy group and a halide group, more preferably a chloride or bromide; $R'_1$, $R'_2$ and $R'_3$ preferably represent an aryl or an alkyl, more preferably an alkyl, wherein alkyl is defined as any compound which is derivable from an alcohol by eliminating the alcoholic function, including arylalkyl, with the proviso that $R'_1$, $R'_2$ and $R'_3$ cannot simultaneously be hydrogen; preferably only one of $R'_1$, $R'_2$ or $R'_3$ represents hydrogen and more preferably none of $R'_1$, $R'_2$ or $R'_3$ represents hydrogen; n represents an integer from 1 to 2; M preferably represents a low atomic radius alkali metal, more preferably lithium or sodium, with the proviso that if the $(CO)_nX_2$ is phosgene, diphosgene or triphosgene and the complexing agent is a tertiary monoamine, or an amine selected from 1,4-diazabicyclo(2,2,2)octane, 1,8-diazabicyclo(5,4,0)undec-7-ene, hexamethylenetetramine, N-methylpiperidine or N-ethylpiperidine then the alkali metal is lithium or sodium, preferably sodium; the sum of the carbon atoms of $R'_1$, $R'_2$ and $R'_3$ is preferably less than or equal to 25 and is more preferably less than or equal to 12.

X is preferably selected so that $R'_2(R'_1)(R'_3)C$-O-COOH has a pKa value greater than the value of HX and more preferably has a leaving group so HX can define the basicity of $X^-$. HX preferably has a pKa less than or equal to 2 and is preferably selected from a hydrogen halide, preferably hydrogen bromide and more preferably hydrogen chloride.

Tert-butyl pyrocarbonate is formed, for example, by carbonation of tert-butylate. The tert-butyl pyrocarbonate is preferably an alkali metal salt and more preferably a sodium salt (e.g., M=Na). The carbonation can be carried out in situ; in other words, the process of the invention can be carried out in one reaction pot without any need to purify the pyrocarbonate before proceeding to obtain the dialkyl dicarbonate.

The complexing agents which can be used are preferably selected from compounds which contain either at least one amine group or at least two ether groups. The at least one amine and at least two ether groups are individually selected so that a complexing agent is formed. The complexing agent is preferably bidentate, more preferably tridentate. The ether and amine groups are preferably separated by at least one and not more than 4 atoms, preferably separated by 2 atoms, and more preferably separated by 3 atoms. The separating atoms are generally carbon atoms.

These atoms are situated so as to ensure coordination when they are linked to one another so that they may form compounds which are complex-forming. In one preferred embodiment the compound is a ring structure having two branches wherein at least one of the branches preferably comprises at least three chain members and the other branch comprises at least two chain members.

The amine groups for use in the present invention must be substantially incapable of reacting with phosgene or oxalyl halides or the like. The amine groups are preferably tertiary amine groups.

The complexing agents preferably have from 3 to 75 carbon atoms and more preferably 6 to 39 carbon atoms.

The complexing agents must be of a bulk and mobility so that the bidentate, tridentate and polydentate structures shall be complex-forming. 1,4-diaza(2,2,2-)bicyclooctane is not of a required bulk and mobility and this accounts for the poor result obtained in Comparative Example B set forth, infra.

Generally, this restriction can be satisfied by avoiding bicyclic systems which have less than or equal to 8 chain members, particularly where the bridgeheads are the atoms which ensure the coordination. Compounds of this type such as diazabicyclooctane, diazabicycloheptane and lower homologs, and to a lesser extent diazabicyclononane, are to be avoided.

Generally, it is preferable to avoid bicyclic systems where the bridgeheads are the atoms which ensure the coordination and in which 2 of the branches, exclusive of the bridgeheads, have less than or equal to 2 chain members, preferably less than or equal to 3 chain members, if the third branch has a length of less than 7 chain members.

The bidentate, preferably with at least one amine group, is highly preferred for phosgene and its derivatives, but not for oxalyl halides and its equivalents The complexing agents which can be used are preferably selected from three classes of complexing agents including oxygenated tertiary amines, cryptands and chalcogene-containing (chalcogenes are the elements of Column VI of the Periodic Table), preferably oxygenated or sulfur-containing, cyclic or macrocyclic compounds, preferably polyethers.

The first class are complexing agents of the general formula:

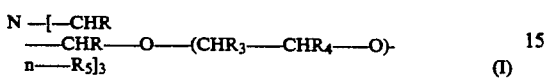

in which n is an integer greater than or equal to about 0 and less than or equal to about 10 ($0 < n < 10$), $R_1$, $R_2$, $R_3$ and $R_4$, which are identical or different, denote a hydrogen atom or an alkyl radical having from 1 to 4 carbon atoms and $R_5$ denotes an alkyl or cycloalkyl radical having from 1 to 12 carbon atoms, a phenyl radical or a radical of the formula $—C_mH_{2m}—C_6H_5$, or $C_mH_{2m+1}—C_6H_4—$, m being from about 1 to about 12.

The second class of complexing agents, the cryptands, are preferably cyclic polyethers preferably having from 6 to 30 atoms in the ring and preferably having from 2 to 10 —O—X units in which X is either —$CHR_6$—$CHR_7$— or —$CHR_6$—$CHR_8$—$CR_9R_7$—, $R_6$, $R_7$, $R_8$ and $R_9$, which are identical or different, being a hydrogen atom or an alkyl radical having from 1 to 4 carbon atoms. One of the X's can be —$CHR_6$—$CHR_8$—$CR_9R_7$— when the —O—X units include a —O—$CHR_6$—$CHR_7$ group. The cyclic polyether is preferably a macrocyclic polyether having more preferably from 15 to 30 atoms in the ring and having more preferably 4 to 10 —O—X units.

The cyclic ethers which can be used in the process according to the invention include dioxane or macrocyclic ethers generally referred to as "crown ethers". These crown ethers are described in French Patent 69/43,879, published under the No. 2,026,481 and specifically incorporated by reference herein.

Representative crown ethers capable of being used in the invention are:

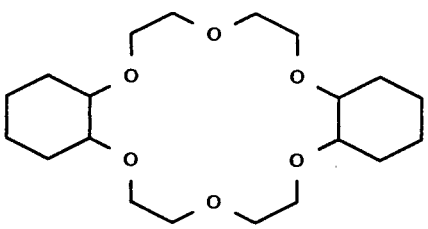

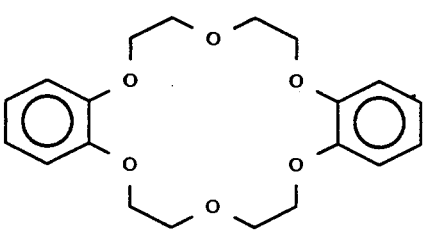

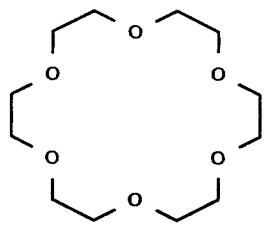

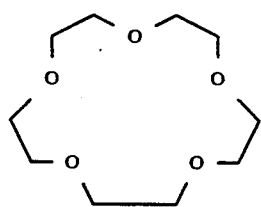

The third class of complexing agents, the chalcogene-containing cyclic or macrocyclic compounds, preferably polyethers, are preferably compounds of the formula:

$$R_{10}—Y—[A—D]_p—A—Y—R_{10} \quad \text{IIa}$$

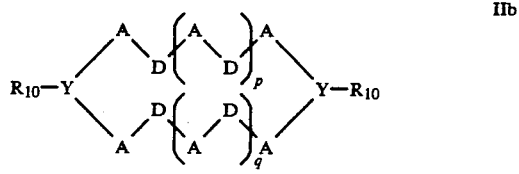  IIb

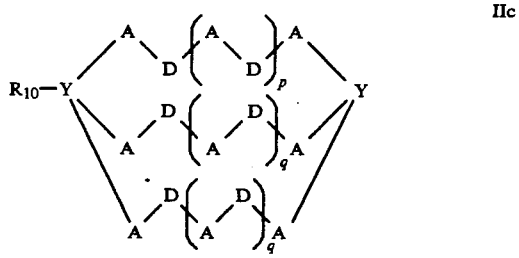  IIc in which:

Y denotes O, N or P,

A denotes an alkylene group having from about 1 to 3 carbon atoms,

D denotes O, S or N—$R_{11}$ where $R_{11}$ denotes an alkyl radical having from about 1 to 6 carbon atoms, and $R_{10}$ can be an alkyl radical having from about 1 to 6 carbon atoms, and p, q and r, which are identical or different, are integers between 1 and 5.

Examples of complexing agents of the third type are described in French Patent 70/21,079, published under number 2,052,947 and specifically incorporated herein by reference. Compounds of this type which are suitable for use in the process of the invention are:

$$CH_3—O—CH_2—CH_2—O—CH_2—CH_2—OCH_3$$

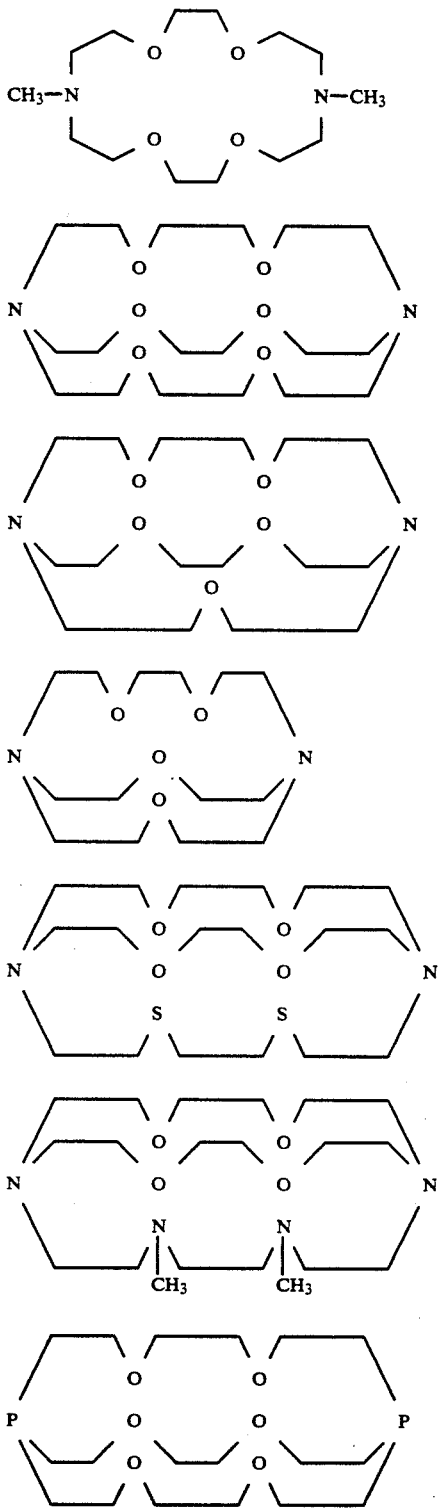

According to one preferred embodiment of the invention, the complexing agent employed is of formula (I), and $R_1$, $R_2$, $R_3$ and $R_4$ denote a hydrogen atom or a methyl radical, $R_5$ and n have the same meaning as above.

Among these preferred complexing agents, it is more preferred to use complexing agents in which n is greater than or equal to 0 and less than or equal to 6 and in which $R_5$ denotes an alkyl radical having from 1 to 4 carbon atoms.

Preferred complexing agents include, tri(3-oxabutyl)amine of formula $$N-(CH_2-CH_2-O-CH_3)_3$$

tris(3-oxaheptyl) amine of formula $$N-(CH_2-CH_2-O-C_4H_9)_3$$

tris(3,6-dioxaheptyl)amine of formula $$N-(CH_2-CH_2-O-CH_2-CH_2-O-CH_3)_3$$

tris(3,6,9-trioxadecyl)amine of formula $$N-(CH_2-CH_2-O-CH_2\text{-}CH_2-O-CH_3)_3$$

tris(3,6-dioxaoctyl)amine of formula $$N-(CH_2-CH_2-O-CH_2-CH_2-OC_2H_5)_3$$

tris(3,6,9-trioxaundecyl)amine of formula $$N-(CH_2-CH_2-O-CH_2-CH_2-O-CH_2-CH_2-O-C_2H_5)_3$$

tris(3,6-dioxanonyl)amine of formula $$N-(CH_2-CH_2-O-CH_2-CH_2-O-C_3H_7)_3$$

tris(3,6,9-trioxadodecyl)amine of formula $$N-(CH_2-CH_2-O-CH_2-CH_2-CH_2-O-C_3H_7)_3$$

tris(3,6-dioxadecyl)amine of formula $$N-(CH_2-CH_2-O-CH_2-CH_2-O-C_4H_9)_3$$

tris(3,6,9-trioxatridec-vl)amine of formula $$N-(CH_2-CH_2-O-CH_2-CH_2-O-CH_2-CH_2-O-C_4H_9)_3$$

tris(3,6,9,12-tetraoxatridecyl)amine of formula $$N-(CH_2-CH_2-O-(CH_2-CH_2-O-)_3-CH_3)_3$$

tris(3,6-dioxa-4-methylheptyl-)amine of formula $$N-(CH_2-CH_2-O-CH_3CHCH_3-CH_2-O-CH_3)_3 \text{ and}$$

tris(3,6-dioxa-2,4-dimethylheptyl)amine of formula $$N-CH_2-CHCH_3\text{-}O\text{-}CHCH_3-CH_2-O-CH_3)_3$$

Among the preferred compounds of formula (I), it is most preferred to use tris(3,6-dioxaheptyl)amine (or $TDA_1$).

Preparation of these complexing agents has been described in French Patent Application 79/05,438, published under the No. 2,450,120 and specifically incorporated by reference herein. According to another preferred embodiment of the process of the invention, an alkali metal tert-butylate, preferably sodium tert-butylate, is contacted with carbon dioxide, and phosgene, diphosgene or triphosgene is subsequently added.

temperature The orange product obtained was analyzed by gas chromatography.

| TEST | Period of phosgene introduction | Period at 35° C. | Period at 55° C. | Phosgene quantity (moles) | $TDA_1$ (ml) | RY % |
|---|---|---|---|---|---|---|
| Comparative A | 2 h 30 min | 2 h 30 min | 1 h | 0.102 | 0 | 31 |
| Example 1 | 2 h 30 min | 2 h 30 min | 1 h | 0.078 | 3 | 58 |
| Example 2 | 2 h 30 min | 2 h 30 min | 0 | 0.097 | 3 | 41 |

The complexing agent may be introduced at any time. The introduction may be made prior to the carbonation of the tertbutylate or before the introduction of the phosgene, diphosgene or triphosgene.

According to yet another preferred embodiment of the process, the phosgene, diphosgene or triphosgene is initially introduced and the tert-butyl pyrocarbonate is subsequently added. The complexing agent can be added at any time.

The reaction can be carried out in any solvent, regardless of the nucleophilicity of the medium. Among the preferred solvents are aromatic hydrocarbon derivatives, such as, benzene,
xylenes,
toluene, and
oxygenated solvents, for example, dioxane and dimethyl ethers of ethylene glycol or of polyethylene glycols.

A preferred molar quantity of $(CO)_nX_2$ as defined above is between about 0.3 and 1 times the amount of alkyl pyrocarbonate employed.

The preferred molar quantity of complexing agent is at least 1 time the amount of the pyrocarbonate employed and preferably not greater than 5 times the amount of the pyrocarbonate employed.

The preferred reaction temperature is between about $-10°$ C. and 60° C.

These and other features and advantages of the present invention will be described more completely with reference to the following examples, which in no case may be regarded as limiting the invention.

DETAILED DESCRIPTION OF THE PREFERRED EMBODIMENT

Examples 1 and 2 and Comparative Test A

These examples set forth the general process of operation according to the invention and display the influence of the quantity of $TDA_1$, on the yield of the product.

12.8 g of sodium tert-butylate (0.075 moles) and 150 ml of dry toluene were charged into a 250 ml reactor. $CO_2$ was introduced at room temperature over a period of about 30 minutes and resulted in the evolution of heat. The introduction was carried out over thirty minutes. The introduction of $CO_2$ was is temperature $TDA_1$ was added. After the addition of the $TDA_1$, phosgene was added over a period of about 2 hour and 30 minutes. The reaction mixture, which was very thick, was allowed to return to 35° C. and was stirred for about 2 hours and 30 minutes. The reaction mixture was then optionally stirred for an additional 1 hour at 55° C.

After cooling the reaction mixture, 100 ml of ice water were added. The organic phase was washed three times with 100 ml of water each time, and then dried over 15 g of sodium sulphate by evaporation at room RY is defined as the reaction yield based on the material introduced and can be set forth as follows:

$$\frac{\text{quantity of product obtained (moles)}}{\text{quantity of tert-butylate introduced (moles)}} \%$$

Example 3

The method was performed as set forth in Example 1. 0.075 moles of sodium tert-butylate, 0.112 moles of phosgene, 150 ml of toluene and 3 ml of $TDA_1$ (0.0015 moles) were charged into a 250 ml reactor. Carbonation was carried out at 10° C. and the reaction temperature was then increased to 55° C. At this temperature, phosgene was introduced over a period of about 2 hours and 30 minutes. The reaction proceeded at this temperature for 3 about A reaction yield of di-tert-butyl dicarbonate of 66% was obtained.

Example 4

The method was performed as in Example 1. 0.13 moles of sodium tert-butylate (tBuONa), 0.0167 moles of triphosgene (that is 0.0501 moles of phosgene), 75 ml of toluene, and 0.015 moles of $TDA_1$ were charged into a 250 ml reactor. Carbonation was carried out at 10° C. After the introduction of triphosgene, the reaction proceeded at 20° C. for about 5 hours and 30 minutes.

A reaction yield of $BOC_2O$ of 51 % was obtained. In this example, the reaction yield was calculated based upon the triphosgene introduced, expressed as phosgene

Example 5

The method was performed as in Example 1. 0.13 moles of sodium tert-butylate (tBuONa), 0.025 moles of diphosgene (that is 0.0500 moles of phosgene), 75 ml of toluene, and 0.015 moles of $TDA_1$ were charged into a 250 ml reactor. Carbonation proceeded at 20° C. for about 5 hours and 30 minutes.

A reaction yield of $BOC_2O$ of 50% was obtained. In this example the reaction yield was calculated based upon the diphosgene introduced, expressed as phosgene.

Example 6

12.8 g of tBuONa (0.13 mole) and toluene were introduced into a 250 ml reactor and $CO_2$ was bubbled in at 5° C. for a period of about 30 minutes, to form tertiary butyl pyrocarbonate. After stopping the introduction of the $CO_2$, 5 g of $TDA_1$ were added. 6.6 g of oxalyl chloride (0.051 mole) were added at 5° C. over a period of about 15 minutes The temperature was allowed to return to normal and the mixture was stirred for about 4 hours and 30 minutes. After treatment, as exemplified in Example 1, 7.6 g of solution were obtained, the solution was analyzed by gas phase chromatography, and found to contain 79% of BOC$_2$O which represents a yield of 54% relative to the amount of oxalyl chloride introduced.

Example 7

This example is a synthesis of BOC$_2$P from oxalyl chloride in the presence of diisopropylethylamine.

75 ml of toluene, 12.8 g of tBuONa (130 mM) and 3 ml of diisopropylethylamine were introduced into a 250 ml reactor. CO$_2$ was introduced at room temperature, for a period of about 30 minutes, until the flow rate of CO$_2$ at the outlet was identical to the flow rate of CO$_2$ at the inlet.

After cooling the mixture to 5° C, 6.4 g of oxalyl chloride (42.8 mM) dissolved in 30 ml of toluene was added over a period of about 20 minutes. The mixture was allowed to return to room temperature, and it is stirred for about 5 hours.

After treatment, as exemplified in Example 1, 5.05 g of liquid were obtained. The solution was analyzed by NMR and found to contain 30% of BOC$_2$O, which represents a yield of 10% relative to the amount of oxalyl chloride introduced.

Comparative Example B 7.5 g of tBuONa (75 mM), 1.7 g of 1,4-diazabicyclo(2,2,2)octane (15 mM) and 75 ml of toluene were introduced into a 250 ml reactor. CO$_2$ was introduced at room temperature for a period of about 30 minutes, until the flow rate of CO$_2$ at the outlet was identical to the flow rate of CO$_2$ at the inlet.

At room temperature, 11.9 g of phosgene (120 mM) were introduced for a period of about 2 hours. The apparatus was then purged with nitrogen while heating the reaction mixture to 55° for about 2 hours.

After cooling and treatment as exemplified in Example 1, 9.5 g of a white liquid were obtained. The liquid was analyzed and found to contain 4.6% of BOC$_2$O, which corresponds to a yield of 1% relative to the sodium tert-butylate.

Comparative Example C 12.8 g of tBuONa (0.13 mole) and toluene were introduced into a 250 ml reactor. CO$_2$ was bubbled into the reactor at 5° C. for about 30 minutes, to form tertiary butyl pyrocarbonate. 6.6 g of oxalyl chloride (0.051 mole) were added at 5° C. over a period of about 15 minutes. The temperature was allowed to return to normal, and the mixture was stirred for about 4 hours and 30 minutes. After treatment, as exemplified in Example 1, 13.9 g of a solution were obtained. The solution was analyzed by gas phase chromatography and found to contain 2.6% of BOC$_2$O, representing a yield of 3.2% relative to the amount of oxalyl chloride introduced.

We claim:

1. A process for the preparation of a secondary or tertiary dialkyl dicarbonate comprising, contacting an alkali metal salt of an alkyl carbonate half ester and (CO)$_n$X$_2$ wherein X is a leaving group and n is an integer from 1 to 2, in the presence of an effective amount of a complexing agent with the proviso that if said (CO)$_n$X$_2$ is phosgene, diphosgene or triphosgene and said complexing agent is a tertiary monoamine, or an amine selected from 1,4-diazabicyclo(2,2,2) octane, 1,8-diazabicyclo (5,4,0)undec-7-ene, hexamethylenetetramine, N-methylpiperidine or N-ethylpiperidine then the alkali metal is selected from sodium or lithium, wherein said complexing agent is selected from compounds which contain either at least one amine group or at least two ether groups with the proviso that if only ether groups are present, the complexing agent is tridentate.

2. The process of claim 1 wherein in said (CO)$_n$X$_2$, X represents an acyloxy group.

3. The process of claim 2, wherein the alkali metal is selected from lithium and sodium.

4. The process of claim 2, wherein the alkyl-carbonate half ester is a sodium salt.

5. The process of claim 2, wherein the reaction is carried out in an aromatic solvent.

6. The process of claim 5, wherein the aromatic solvent is toluene.

7. The process of claim 2, wherein the complexing agent is selected from oxygenated tertiary amines, chalcogene-containing cyclic or polyethers, and cryptands.

8. The process according to claim 7, wherein the complexing agent is an oxygenated tertiary amine of the formula:

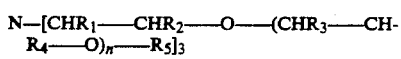

in which n is an integer greater than or equal to about 0 and less than or equal to about 10 (0≦n≦10), R$_1$, R$_2$, R$_3$ and R$_4$, which are identical or different, denote a hydrogen atom or an alkyl radical having from 1 to 4 carbon atoms and R$_5$ denotes an alkyl or cycloalkyl radical having from 1 to 12 carbon atoms, a phenyl radical or a radical of formula —C$_m$H$_{2m}$—C$_6$H$_5$, or C$_m$H$_{2m+1}$—C$_6$H$_4$—, m being from about 1 to about 12.

9. The process of claim 7, wherein the complexing agent is a chalcogene-containing cyclic or polyether which corresponds to the following formula II(a), II(b) or II(c),

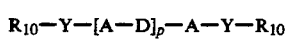

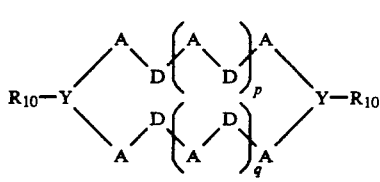

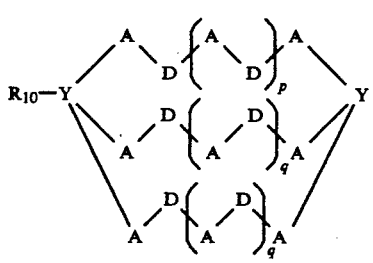

in which

Y denotes O, N or P,

A denotes an alkylene group having from 1 to 3 carbon atoms,

D denotes O, S or N—R$_{11}$ where R$_{11}$ denotes an alkyl radical having from 1 to 6 carbon atoms, $R_{10}$ denotes an alkyl radical having from 1 to 6 carbon atoms, and p, q and r, which are identical or different, are integers between 1 and 5.

10. The process of claim 7, wherein the complexing agent is a cryptand.

11. The process of claim 8, wherein the oxygenated amine is trisdioxaheptylamine.

12. The process of claim 9, wherein the polyether is diethylene glycol dimethyl ether.

13. The process of claim 1 wherein said $(CO)_nX_2$ is a diacid dihalide.

14. The process of claim 13, wherein the alkali metal is selected from lithium and sodium.

15. The process of claim 14, wherein the alkyl carbonate half ester is a sodium salt.

16. The process of claim 13, wherein the reaction is carried out in an aromatic solvent.

17. The process of claim 16, wherein the aromatic solvent is toluene.

18. The process of claim 13, wherein the complexing agent is selected from oxygenated tertiary amines, chalcogene-containing cyclic polyethers, and cryptands.

19. The process according to claim 18, wherein the complexing agent is an oxygenated tertiary amine of the formula:

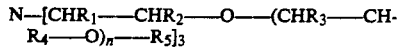
N—[CHR$_1$——CHR$_2$——O——(CHR$_3$——CHR$_4$——O)$_n$——R$_5$]$_3$ in which n is an integer greater than or equal to about 0 and less than or equal to about 10 ($0 \leq n \leq 10$), $R_1$, $R_2$, $R_3$ and $R_4$, which are identical or different, denote a hydrogen atom or an alkyl radical having from 1 to 4 carbon atoms and $R_5$ denotes an alkyl or cycloalkyl radical having from 1 to 12 carbon atoms, a phenyl radical or a radical of formula —$C_mH_{2m}$—$C_6H_5$, or $C_mH_{2m+1}$—$C_6H_4$—, m being from about 1 to about 12.

20. The process of claim 18, wherein the complexing agent is a chalcogene-containing cyclic or macrocyclic polyether which corresponds to the following formula II(a), II(b) or II(c),

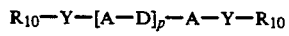
$R_{10}$—Y—[A—D]$_p$—A—Y—$R_{10}$     IIa

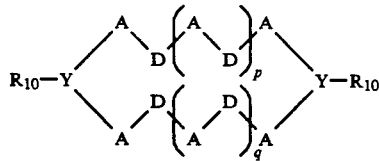
IIb

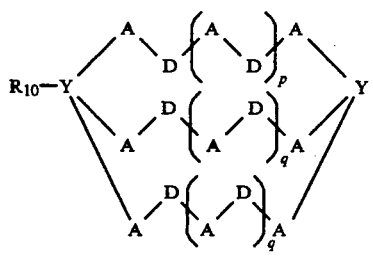
IIc in which
Y denotes O, N or P,
A denotes an alkylene group having from 1 to 3 carbon atoms, D denotes O, S or N-$R_{11}$ where $R_{11}$ denotes an alkyl radical having from 1 to 6 carbon atoms, $R_{10}$ denotes an alkyl radical having from 1 to 6 carbon atoms, and p, q and r, which are identical or different, are integers between 1 and 5.

21. The process of claim 18, wherein the complexing agent is a cryptand.

22. The process of claim 19, wherein the oxygenated amine is trisdioxaheptylamine.

23. The process of claim 20, wherein the polyether is diethylene glycol dimethyl ether.

24. The process of claim 1, wherein in said $(CO)_nX_2$, X represents a halide.

25. The process of claim 24, wherein the alkali metal is selected from lithium and sodium.

26. The process of claim 24, wherein the alkyl carbonate half ester is a sodium salt.

27. The process of claim 24, wherein the reaction is carried out in an aromatic solvent.

28. The process of claim 27, wherein the aromatic solvent is toluene.

29. The process of claim 24, wherein the complexing agent is selected from oxygenated tertiary amines, chalcogene-containing cyclic polyethers, and cryptands.

30. The process according to claim 31, wherein the complexing agent is an oxygenated tertiary amine of the formula:

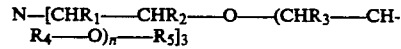
N—[CHR$_1$——CHR$_2$——O——(CHR$_3$——CHR$_4$——O)$_n$——R$_5$]$_3$ in which n is an integer greater than or equal to about 0 and less than or equal to about 10 ($0 \leq n \leq 10$), $R_1$, $R_2$, $R_3$ and $R_4$, which are identical or different, denote a hydrogen atom or an alkyl radical having from 1 to 4 carbon atoms and $R_5$ denotes an alkyl or cycloalkyl radical having from 1 to 12 carbon atoms, a phenyl radical or a radical of formula —$C_mH_{2m}$—$C_6H_5$, or $C_mH_{2m+1}$—$C_6H_4$—, m being from about 1 to about 12.

31. The process of claim 29, wherein the complexing agent is a chalcogene-containing cyclic or macrocyclic polyether which corresponds to the following formula II(a), II(b) or II(c),

$R_{10}$—Y—[A—D]$_p$—A—Y—$R_{10}$     IIa

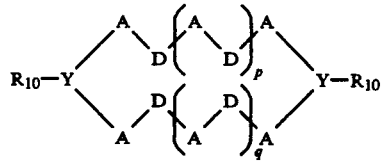
IIb

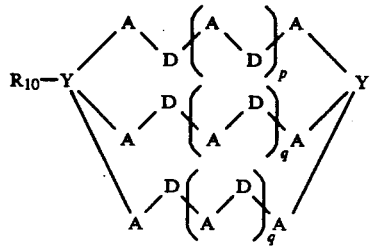
IIc in which
Y denotes O, N or P,

A denotes an alkylene group having from 1 to 3 carbon atoms,

D denotes O, S or N-$R_{11}$ where $R_{11}$ denotes an alkyl radical having from 1 to 6 carbon atoms, $R_{10}$ denotes an alkyl radical having from 1 to 6 carbon atoms, and p, q and r, which are identical or different, are integers between 1 and 5.

32. The process of claim 29, wherein the complexing agent is a cryptand.

33. The process of claim 30, wherein the oxygenated amine is trisdioxaheptylamine.

34. The process of claim 31, wherein the polyether is diethylene glycol dimethyl ether.

35. A process for the preparation of di-tert-butyl dicarbonate comprising, contacting an alkali metal salt of di-tert-butyl carbonate half ester with phosgene, diphosgene or triphosgene, in the presence of an effective amount of a complexing agent with the proviso that if said complexing agent is a tertiarymonoamine, or an amine selected from 1,4-diazabicyclo (2,2,2) octane, 1,8-diazabicyclo (5,4,0)-undec-7-ene, hexamethylenetetramine, N-methylpiperidine or N-ethylpiperidine then the alkali metal is selected from sodium or lithium, wherein said complexing agent is selected from compounds which contain either at least one amine group or at least two ether groups with the proviso that if only ether groups are present, the complexing agent is tridentate.

36. The process of claim 35, wherein the di-tert-butyl carbonate half ester is a sodium salt.

37. The process of claim 35, wherein the reaction is carried out in an aromatic solvent.

38. The process of claim 39, wherein the aromatic solvent is toluene.

39. The process of claim 35, wherein the complexing agent is selected from oxygenated tertiary amines, chalcogene-containing cyclic polyethers, and cryptands.

40. The process according to claim 39, wherein the complexing agent is an oxygenated tertiary amine of the formula:

$$N-[CHR_1-CHR_2-O-(CHR_3-CHR_4-O)_n-R_5]_3$$

in which n is an integer greater than or equal to about 0 and less than or equal to about 10 ($0 \leq n \leq 10$), $R_1$, $R_2$, $R_3$ and $R_4$, which are identical or different, denote a hydrogen atom or an alkyl radical having from 1 to 4 carbon atoms and $R_5$ denotes an alkyl or cycloalkyl radical having from 1 to 12 carbon atoms, a phenyl radical or a radical of formula —$C_mH_{2m}$—$C_6H_5$, or $C_mH_{2m+1}$—$C_6H_4$—, m being from about 1 to about 12.

41. The process of claim 39, wherein the complexing agent is a chalcogene-containing cyclic or macrocyclic polyether which corresponds to the following formula II(a), II(b) or II(c),

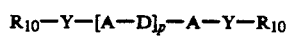
IIa

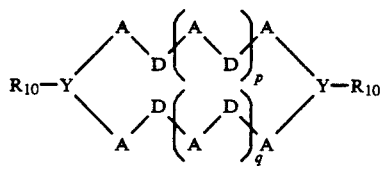
IIb

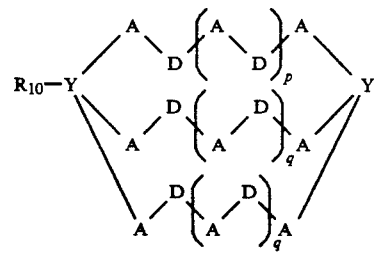
IIc in which

Y denotes O, N or P,

A denotes an alkylene group having from 1 to 3 carbon atoms,

D denotes O, S or N-$R_{11}$ where $R_{11}$ denotes an alkyl radical having from 1 to 6 carbon atoms, $R_{10}$ denotes an alkyl radical having from 1 to 6 carbon atoms, and p, q and r, which are identical or different, are integers between 1 and 5.

42. The process of claim 39, wherein the complexing agent is a cryptand.

43. The process of claim 40, wherein the oxygenated amine is trisdioxaheptylamine.

44. The process of claim 43, wherein the polyether is diethylene glycol dimethyl ether.

45. A process for the preparation of secondary or tertiarydialkyl dicarbonate comprising, contacting an alkali metal tertiary or secondary butylate with carbon dioxide and $(CO)_nX_2$ in the presence of an effective amount of a complexing agent, wherein said complexing agent is selected from compounds which contain either at least one amine group or at least two ether groups with the proviso that is only ether groups are present, the complexing agent is tridentate, wherein the secondary or tertiary dialkyl dicarbonate is formed without the intermediate purification of a carbonate half ester reactant.

46. The process of claim 45, wherein the alkali metal butylate is a sodium salt.

47. The process of claim 45, wherein the reaction is carried out in an aromatic solvent.

48. The process of claim 47, wherein the aromatic solvent is toluene.

49. The process of claim 45, wherein the complexing agent is selected from oxygenated tertiary amines, chalcogene-containing cyclic polyethers, and cryptands.

50. The process according to claim 49, wherein the complexing agent is an oxygenated tertiary amine of the formula:

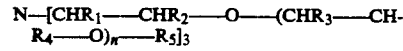

in which n is an integer greater than or equal to about 0 and less than or equal to about 10 ($0 \leq n \leq 10$), $R_1$, $R_2$, $R_3$ and $R_4$, which are identical or different, denote a hydrogen atom or an alkyl radical having from 1 to 4 carbon atoms and $R_5$ denotes an alkyl or cycloalkyl radical having from 1 to 12 carbon atoms, a phenyl radical or a radical of formula —$C_mH_{2m}$—$C_6H_5$, or $C_mH_{2m+1}$—$C_6H_4$—, m being from about 1 to about 12.

51. The process of claim 49, wherein the complexing agent is a chalcogene-containing cyclic or macrocyclic polyether which to the following formula II(a), II(b) or II(c),

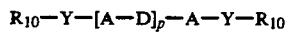
IIa

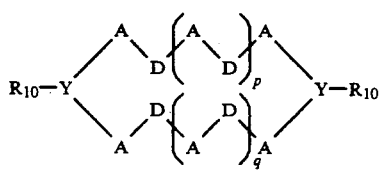
IIb

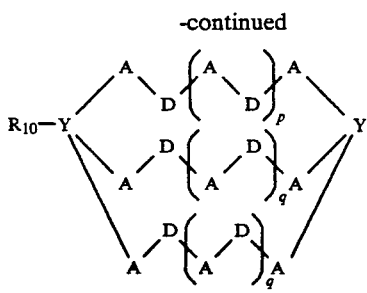
IIc in which
Y denotes O, N or P,
A denotes an alkylene group having from 1 to 3 carbon atoms,
D denotes O, S or N-$R_{11}$ where $R_{11}$ denotes an alkyl radical having from 1 to 6 carbon atoms,
$R_{10}$ denotes an alkyl radical having from 1 to 6 carbon atoms, and p, q and r, which are identical or different, are integers between 1 and 5.

52. The process of claim 49, wherein the complexing agent is a cryptand.

53. The process of claim 50, wherein the oxygenated amine is trisdioxaheptylamine.

54. The process of claim 51, wherein the polyether is diethylene glycol dimethyl ether.

* * * * *

UNITED STATES PATENT AND TRADEMARK OFFICE
CERTIFICATE OF CORRECTION

PATENT NO. : 5,206,407
DATED : April 27, 1993
INVENTOR(S) : Jean Desmurs et al.

It is certified that error appears in the above-indentified patent and that said Letters Patent is hereby corrected as shown below:

Claim 1, column 9, line 68 change "(5,4,0)undec-7-ene" to --(5,4,0)-undec-7-ene--.

Claim 4, column 10, lines 13-14, change "alkyl-carbonate" to --alkyl carbonate--.

Claim 9, column 10, line 38 delete "or".

Claim 35, column 13, line 20 change "tertiarymonoamine" to --tertiary monoamine--.

Claim 45, column 14, line 38 change "is" to --if--.

In the Title, line 2, change "OF" to --OR--.

UNITED STATES PATENT AND TRADEMARK OFFICE
CERTIFICATE OF CORRECTION

PATENT NO. : 5,206,407
DATED : April 27, 1993
INVENTOR(S) : Jean DESMURS et al

It is certified that error appears in the above-indentified patent and that said Letters Patent is hereby corrected as shown below:

Claim 9, column 10, lines 53-62;

Claim 20, column 11, lines 55-64;

Claim 31, column 12, lines 56-65;

Claim 41, column 14, lines 3-12; and

UNITED STATES PATENT AND TRADEMARK OFFICE
CERTIFICATE OF CORRECTION

PATENT NO. : 5,206,407
DATED : April 27, 1993
INVENTOR(S) : Jean DESMURS et al.

It is certified that error appears in the above-indentified patent and that said Letters Patent is hereby corrected as shown below:

Claim 51, column 16, lines 2-11, Formula IIc, change

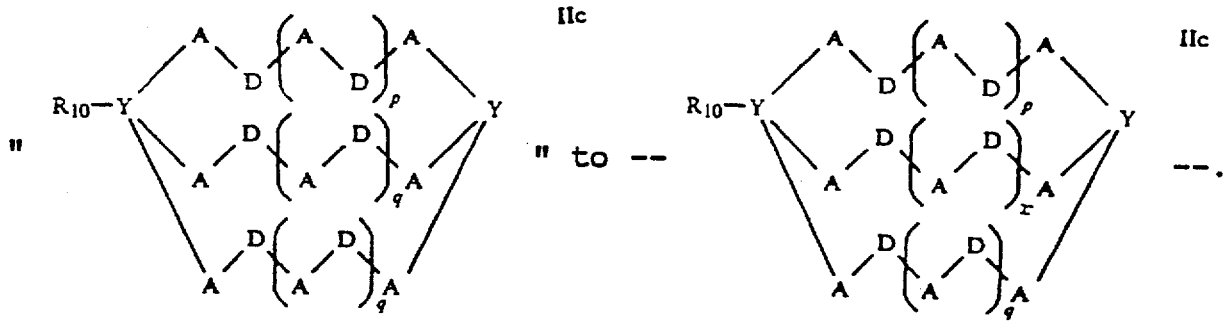

Signed and Sealed this

Eleventh Day of April, 1995

Attest:

BRUCE LEHMAN

Attesting Officer     Commissioner of Patents and Trademarks